(12) United States Patent
Carls et al.

(10) Patent No.: US 7,931,681 B2
(45) Date of Patent: Apr. 26, 2011

(54) ANTI-BACKOUT MECHANISM FOR AN IMPLANT FASTENER

(75) Inventors: Thomas Carls, Memphis, TN (US); Eric C. Lange, Collierville, TN (US); Kent M. Anderson, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 582 days.

(21) Appl. No.: 11/105,656

(22) Filed: Apr. 14, 2005

(65) Prior Publication Data
US 2006/0235399 A1 Oct. 19, 2006

(51) Int. Cl.
A61B 17/80 (2006.01)

(52) U.S. Cl. ........................................................ 606/290

(58) Field of Classification Search ................ 606/61, 606/69, 280, 70, 71, 281–299, 309–312
See application file for complete search history.

(56) References Cited

U.S. PATENT DOCUMENTS

| | | | |
|---|---|---|---|
| 5,057,111 A | 10/1991 | Park | |
| 5,269,784 A | 12/1993 | Mast | |
| 5,578,034 A * | 11/1996 | Estes | 606/61 |
| 5,797,912 A | 8/1998 | Runciman et al. | |
| 5,954,722 A * | 9/1999 | Bono | 606/281 |
| 6,077,262 A | 6/2000 | Schlapfer et al. | |
| 6,187,005 B1 | 2/2001 | Brace et al. | |
| 6,224,631 B1 * | 5/2001 | Kohrs | 623/17.11 |
| 6,261,291 B1 * | 7/2001 | Talaber et al. | 606/281 |
| 6,331,179 B1 | 12/2001 | Freid et al. | |
| 6,602,255 B1 * | 8/2003 | Campbell et al. | 606/69 |
| 6,656,181 B2 | 12/2003 | Dixon et al. | |
| 6,890,334 B2 | 5/2005 | Brace et al. | |
| 6,902,565 B2 | 6/2005 | Berger et al. | |
| 7,018,418 B2 * | 3/2006 | Amrich et al. | 623/23.5 |
| 7,195,633 B2 * | 3/2007 | Medoff et al. | 606/309 |
| 2001/0014807 A1 | 8/2001 | Wagner et al. | |
| 2001/0021851 A1 | 9/2001 | Eberlein et al. | |
| 2002/0045898 A1 * | 4/2002 | Freid et al. | 606/61 |
| 2003/0078583 A1 * | 4/2003 | Biedermann et al. | 606/69 |
| 2003/0083658 A1 * | 5/2003 | Hawkes et al. | 606/61 |
| 2003/0153919 A1 * | 8/2003 | Harris | 606/69 |
| 2003/0187440 A1 * | 10/2003 | Richelsoph et al. | 606/61 |
| 2004/0006342 A1 | 1/2004 | Altarac et al. | |
| 2004/0127899 A1 | 7/2004 | Konieczynski et al. | |
| 2004/0267261 A1 | 12/2004 | Derouet | |
| 2005/0027296 A1 | 2/2005 | Thramann et al. | |
| 2005/0059970 A1 | 3/2005 | Kolb | |
| 2005/0169958 A1 * | 8/2005 | Hunter et al. | 424/423 |

FOREIGN PATENT DOCUMENTS

DE 100 39 767 A1 1/2000

(Continued)

*Primary Examiner* — Eduardo C Robert
*Assistant Examiner* — Tara R Carter

(57) ABSTRACT

A retaining mechanism engages a bone fastener to a bone plate as the bone fastener is positioned through a retaining mechanism in a plate hole while preserving multi-axial capabilities of the fastener relative to the plate during insertion of the fastener. When the head of the fastener is positioned adjacent the plate, the head can optionally be received in the retaining mechanism and expand the retaining mechanism to fixedly engage the retaining mechanism into locking engagement with the plate and lock the bone fastener in position relative to the plate. In another form, the multi-axial capabilities of the bone screw is preserved or at least partially preserved when the bone fastener is finally positioned in the retaining mechanism.

18 Claims, 2 Drawing Sheets

FOREIGN PATENT DOCUMENTS

| DE | 100 15 734 A1 | 3/2000 |
| EP | 1 250 892 A2 | 4/2002 |
| FR | 2 790 198 A1 | 2/1999 |
| GB | 2 392 096 A | 6/2002 |
| WO | WO 99/05968 | 2/1999 |

* cited by examiner

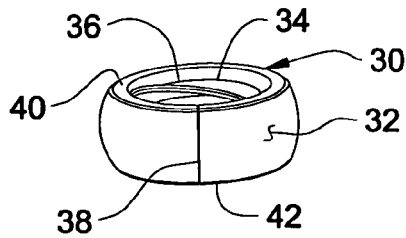
Fig. 6
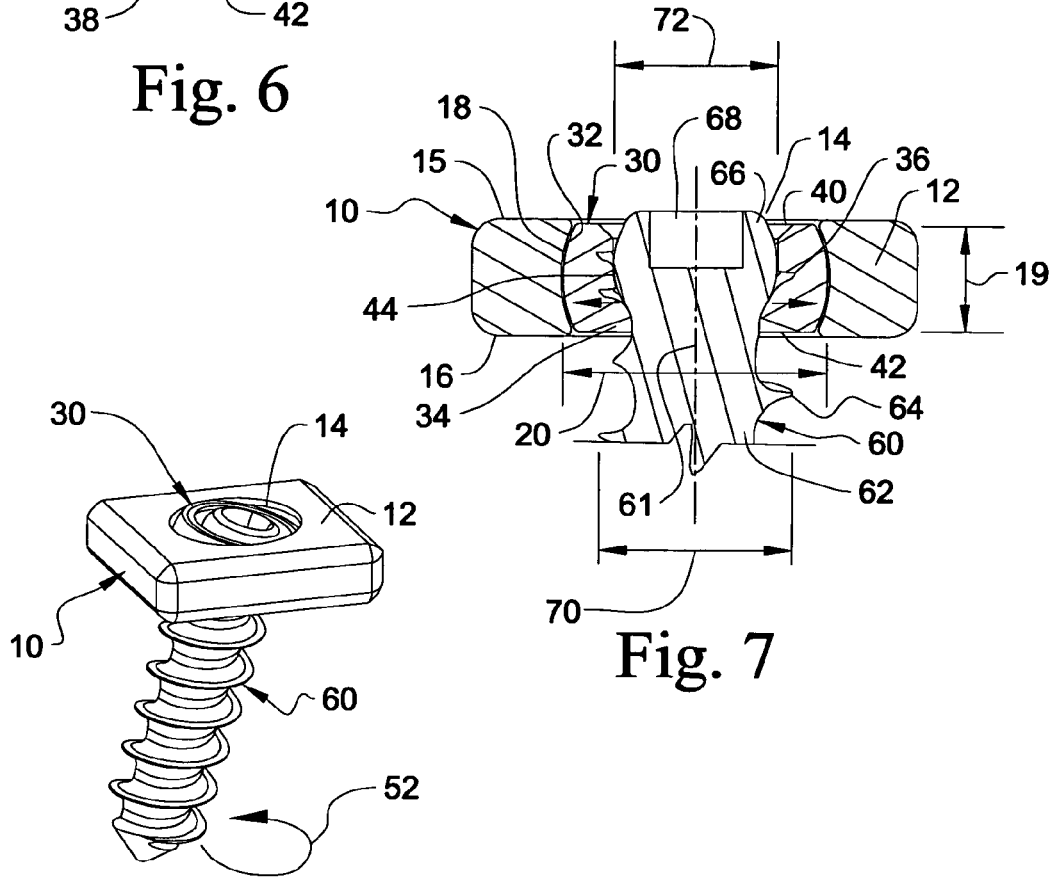
Fig. 8
Fig. 7
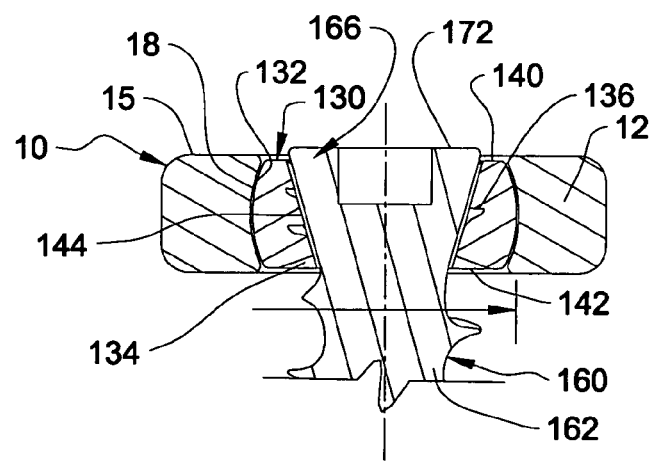
Fig. 9

ANTI-BACKOUT MECHANISM FOR AN IMPLANT FASTENER

BACKGROUND

Bone plates and other implants can be engaged to adjacent bony portions of a bone or of a bony segment to stabilize the bone portions. Fasteners can be used to engage the implant to the bony portions. To prevent the fasteners from backing out of the underlying bone relative to the implant, various retaining devices have been developed for engagement to the implant adjacent to or around the bone fasteners. Some retaining devices are in the form of set screws, washers, arms or flaps that interfere with the bone screw if it moves into contact with the retaining device. These retaining devices block the fasteners to prevent them from backing out of the implant.

SUMMARY

According to one aspect, there is provided a retaining mechanism that engages a bone fastener to an implant as the bone fastener is positioned through a hole of the implant while preserving multi-axial capabilities of the fastener relative to the implant during insertion of the fastener. When the head of the fastener is positioned adjacent the implant, the head can optionally be received in the retaining mechanism and expand the retaining mechanism to fixedly engage the retaining mechanism into locking engagement with the implant and lock the bone fastener in position relative to the implant. In another form, the multi-axial positioning capabilities of the bone fastener relative to the implant is preserved or at least partially preserved when the bone fastener is finally positioned in the retaining mechanism.

According to another aspect, a retaining mechanism for an implant fastener is provided that includes an internally threaded bore that matches the thread profile of a bone fastener positioned therethrough. In another form, the bore is sized to fit between thread turns of the bone fastener as the bone fastener is threaded through the retaining mechanism.

In a further aspect, a bone fastener includes a thread profile with an outer dimension orthogonal to the longitudinal axis of the bone fastener that is greater than an outer dimension of the head of the bone fastener orthogonal to the longitudinal axis. A retaining mechanism coupled to an implant is configured to allow passage of the bone fastener therethrough.

In another aspect, a retaining mechanism retains a bone fastener relative to an implant as the bone fastener is threadingly engaged to the underlying bony structure while preserving multi-axial placement capabilities of the bone fastener relative to the implant.

According to another aspect, there is provided an implant having a hole for receiving a bone fastener. The hole includes concave sidewalls extending between upper and lower surfaces of the implant so that the greatest dimension of the opening is along a centralized portion of the opening between the upper and lower surfaces of the implant. The implant further includes opposite channels adjacent the hole extending from one of the upper or lower surface of the implant to the centralized portion of the hole.

According to a further aspect, a retaining mechanism with a convex outer wall surface profile that matches the concave surface profile of the implant hole is provided to retain bone fasteners in the implant hole. The channels adjacent the implant hole allow the retaining mechanism to be inserted into the implant hole while in an insertion orientation that is rotated 90 degrees relative to its normal, fastener receiving position in the implant hole. In the rotated orientation, the walls of the retaining mechanism are aligned with the channels. The retaining mechanism is guided in this orientation through the channels and into the implant holes until the maximum dimension of the outer surface of the retaining mechanism is aligned with the maximum dimension of the implant hole. The retaining mechanism is then rotated 90 degrees so that it is seated in and captured in the implant hole. The matching concavo-convex profiles of the retaining mechanism and the implant hole prevent the retaining mechanism from passing distally or proximally from the implant hole while in its fastener receiving orientation. The retaining mechanism can be removed by rotating it 90 degrees to its insertion orientation so that its outer surface is aligned with the opposite channels adjacent the implant hole.

These and other aspects of the invention will also be apparent from the following description.

BRIEF DESCRIPTION OF THE FIGURES

FIG. 6 is another perspective view of the retaining mechanism.

FIG. 7 is a sectional view of the plate and retaining mechanism with a bone fastener seated in the retaining mechanism.

FIG. 8 is a perspective view showing the bone fastener seated in the retaining mechanism oriented at a variable angle relative to the bone plate.

FIG. 9 is a sectional view of the plate and another embodiment retaining mechanism and bone fastener seated in the retaining mechanism.

DESCRIPTION OF THE ILLUSTRATED EMBODIMENTS

Figure 1:
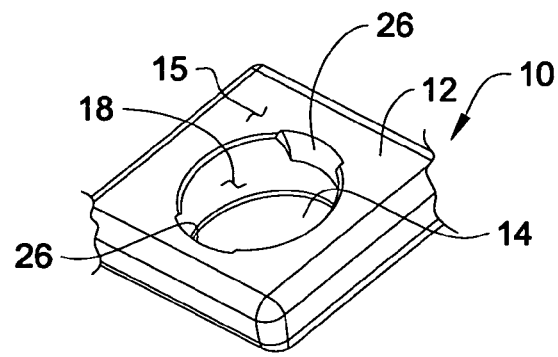
FIG. 1 is a perspective view of a portion of a bone plate.

For the purposes of promoting an understanding of the principles of the invention, reference will now be made to the embodiment illustrated in the drawings and specific language will be used to describe the same. It will nevertheless be understood that no limitation of the scope of the invention is thereby intended. Any such alterations and further modifications in the illustrated device and any such further applications of the principles of the invention as illustrated herein are contemplated as would normally occur to one skilled in the art to which the invention relates.

In FIGS. 1 and 7 there is shown a portion of a bone implant 10 in the form of a plate 12 with a hole 14 extending between and opening at upper and lower surfaces 15, 16. As used herein, lower surface 16 refers to the surface of plate 12 positionable against or adjacent the underlying bony structure to which plate 12 is to be attached. Hole 14 is defined by a wall surface 18 extending between upper and lower surfaces 15, 16. Wall surface 18 in the illustrated embodiment is concavely curved and defines a maximum opening dimension 20 at any location situated between upper and lower surfaces 15, 16 along a centralized portion 19 of hole 14. The dimensions of hole 14 adjacent upper and lower surfaces 15, 16 is less than the maximum hole dimension 20 to prevent retaining mechanism 30 from passing distally or proximally through opening 14 when in its fastener receiving orientation, as shown in FIG. 7.

Plate 12 further includes receiving channels 26 formed therein adjacent hole 14 that are adapted to facilitate placement of retaining mechanism 30 into hole 14. Channels 26 are located opposite one another about hole 14, and extend from upper surface 15 to centralized portion 19 of hole 14. Channels 26 are recessed into plate 12 to form a discontinuity in wall surface 18 of hole 14. These discontinuities provide an opening dimension that is greater than the opening dimension defined by wall 18 about the remaining portion of hole 14.

Figure 2:
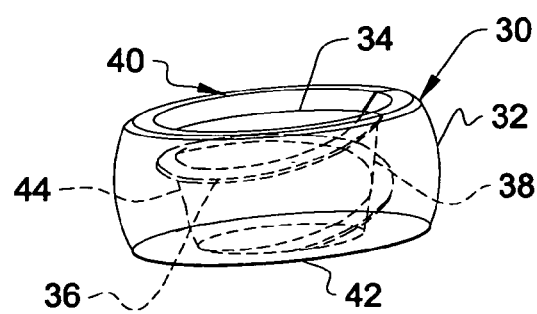
FIG. 2 is a perspective view of a retaining mechanism for a bone fastener.

FIGS. 2 and 6 show a retaining mechanism 30 positionable in hole 14 of plate 12. Retaining mechanism 30 receives a bone fastener 60 (FIGS. 7 and 8) that is to be positioned through hole 14 and retaining mechanism 30 to secure plate 12 to an underlying bony structure. Retaining mechanism 30 extends between the plate and the bone fastener and engages the plate to prevent the fastener from backing out relative to the plate.

In the illustrated embodiment, retaining mechanism 30 is in the form of a bushing with a cylindrical-like body including an outer surface 32 and a bore 34 extending between upper and lower ends 40, 42. Bore 34 is defined at least in part by an inner wall surface 44 having an internal thread profile 36 formed therein. Upper and lower ends 40, 42 can be flush or are recessed relative to the adjacent upper and lower surfaces 15, 16 of plate 12 when retaining mechanism 30 is positioned in hole 14. In another embodiment, one or both of the ends 40, 42 projects outwardly from the adjacent upper or lower surface 15, 16. Bore 34 can be flared adjacent upper and lower ends 40, 42 to facilitate placement of a fastener therethrough.

Figures 3, 4, 5:
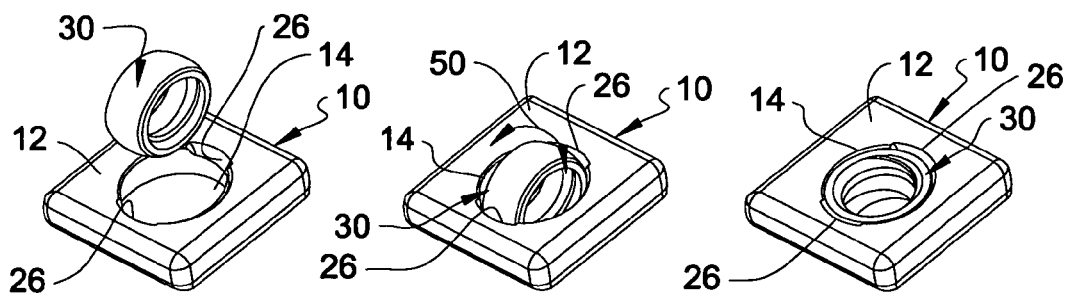
FIG. 3 is a perspective view of the retaining mechanism of FIG. 2 being positioned toward a hole of the bone plate of FIG. 1.
FIG. 4 is a perspective view showing the retaining mechanism bushing positioned in the hole of the bone plate before the retaining mechanism is seated in the plate hole.
FIG. 5 is a perspective showing the retaining mechanism seated in the plate hole to allow passage of a bone fastener therethrough.

FIGS. 3-5 show steps for one technique for positioning retaining mechanism 30 in plate hole 14. As shown in FIG. 7, hole 14 includes a central axis 61 along which fastener 60 and bore 34 of retaining mechanism 30 are aligned when positioned in hole 14. In FIG. 3, retaining mechanism 30 is rotated 90 degrees to an insertion orientation so that bore 34 is transversely oriented to axis 61. Retaining mechanism 30 is guided in this insertion orientation into hole 14 so that outer surface 32 is received in channels 26. Retaining mechanism 30 is advanced distally in channels 26 into hole 14 until retaining mechanism 30 can no longer be advanced as a result of outer surface 32 contacting wall surface 18 along or adjacent the terminal ends of channels 26 at wall surface 18. Retaining mechanism 30 can then be rotated, as indicated by arrow 50 in FIG. 4, to a fastener receiving orientation, as shown in FIG. 5. In the fastener receiving orientation, bore 34 is generally aligned with central axis 61 and opens toward the upper and lower surfaces 15, 16 of plate 12 to receive bone fastener 60. Retaining mechanism 30 can be pivoted in hole 14 to accommodate variable angle fastener placement through hole 14, although fixed engagement is also contemplated.

Other techniques for inserting retaining mechanism 30 are also contemplated. For example, the retaining mechanism can be contracted or otherwise positioned or formed in a reduced size configuration for insertion and thereafter released or expanded for placement in the plate hole. Retaining mechanism 30 can also be force-fit into the plate hole. In still another form, retaining mechanism 30 can be provided in multiple components that are assembled or positioned relative to one another in the plate hole.

The interface between retaining mechanism 30 and the wall surface 18 of plate 12 defining hole 14 is illustrated as rounded surfaces that are formed to be positioned in close relation to one another. Various forms for the adjacent surfaces are contemplated, including concave-convex surfaces defined by rounded, linear or combinations of rounded and linear surfaces; spherically-shaped surfaces, angular surfaces, and any other surface shapes and configurations that would suitably maintain retaining mechanism 30 in engagement with plate 12 at least when fastener 60 is positioned therethrough.

Once retaining mechanism 30 is positioned in plate hole 14 in its fastener receiving orientation, bone fastener 60 can be advanced through retaining mechanism 30 to secure plate 12 to the underlying bony structure. In one embodiment, fastener 60 is a bone screw including a shank 62 having a thread profile 64 therealong and an enlarged head 66 at the proximal end of shank 62. In the illustrated embodiment, head 66 includes a width 72 orthogonal to the longitudinal axis of fastener 60, and width 72 is less than a thread width 70 between the outer crests of thread profile 64. In another embodiment, width 72 of head 66 is the same as or greater than thread width 70.

In use, retaining mechanism 30 is positioned in hole 14 of plate 12 using any of the techniques discussed above. Fastener 60 is aligned over hole 14 so that its distal end can be inserted into bore 34 of retaining mechanism 30. Fastener 60 can be threadingly advanced through retaining mechanism 30 with thread profile 64 threadingly engaging internal thread profile 36 of retaining mechanism 30. When engaged in this fashion, retaining mechanism 30 is prevented from rotating sufficiently in the direction of arrows 50 to align outer surface 32 with channels 26. Thus, retaining mechanism 30 is immovably captured in plate hole 14 with fastener 60. Furthermore, retaining mechanism 30 axially restrains fastener 60 relative to plate 12 even when fastener 60 is not seated with head 66 in bore 34. Retaining mechanism 30 can pivot within hole 14 to allow multi-angle placement capabilities for fastener 60 as it is positioned through plate 10 and driven into the underlying bony structure.

Fastener 60 can be further driven into the underlying bony structure as indicated by arrow 52 in FIG. 8 until head 66 is received in bore 34 in contact with inner wall surface 44 of retaining mechanism 30. To prevent retaining mechanism 30 from rotating during insertion of fastener 60, retaining mechanism 30 can be engaged by the driving instrument or a second instrument to prevent its rotation. Retaining mechanism 30 can be provided with recesses or other features that facilitate such engagement. Retaining mechanism 30 could also be expanded into engagement with the plate hole to maintain its positioning during fastener insertion.

Width 72 of head 66 can be sized relative to the opening formed by inner wall surface 44 to expand retaining mechanism 30 so that outer surface 32 contacts wall surface 18 of plate 12. The expansion of retaining mechanism 30 is facilitated by slot 38, which extends between inner wall surface 44 and outer surface 32.

The provision of internal thread profile 36 allows width 70 of thread profile 64 to be greater than it would be if width 70 were required to fit through bore 34. Greater purchase into the bony material can be achieved by thread profile 64 while the size of hole 14 in plate 10 can be minimized, reducing the relative material reduction in plate 10 and providing increased strength and/or allowing a reduction in size of the plate without a loss in relative strength.

In another embodiment, retaining mechanism 30 is provided without an internal thread profile. Rather, the height between upper and lower ends 40, 42 at least adjacent bore 34 is sized to fit within the spacing between the threads of thread profile 64. Accordingly, fastener 60 can be inserted as above even with thread width 70 greater than the opening provided by bore 34.

When head 66 is in bore 34, retaining mechanism 30 can be expanded to contact wall surface 18 about hole 14 and prevent fastener 60 from backing out relative to plate 12. Fastener 60 can be removed for revision or other purposes by unscrewing it through retaining mechanism 30.

In FIG. 9 there is shown another embodiment retaining mechanism 130 in the form of a bushing with a cylindrical body including an outer surface 132 and a bore 134 extending between upper and lower ends 140, 142. Bore 134 is defined at least in part by an inner wall surface 144 having an internal thread profile 136 formed therein. Upper and lower ends 140, 142 can be flush or are recessed relative to the adjacent upper and lower surfaces 15, 16 of plate 12 when retaining mechanism 130 is positioned in hole 14. In another embodiment, one or both of the ends 140, 142 projects outwardly from the adjacent upper or lower surface 15, 16. Retaining mechanism 130 can be positioned in the plate hole in any manner discussed herein.

Once retaining mechanism 130 is positioned in plate hole 14 in its fastener receiving orientation, a bone fastener 160 can be advanced through retaining mechanism 130 to secure plate 12 to the underlying bony structure. In one embodiment, fastener 160 is a bone screw including a shank 162 having a thread profile 164 therealong and an enlarged head 166 at the proximal end of shank 162. In the illustrated embodiment, head 166 includes a distally tapered outer surface 172 forming a frusto-conical shape extending about the longitudinal axis of fastener 160. The outer width of head 166 along outer surface 172 is less than a thread width between the outer crests of thread profile 164.

Fastener 160 can be threadingly advanced through retaining mechanism 130 with thread profile 164 threadingly engaging internal thread profile 136 of retaining mechanism 130. When engaged in this fashion, retaining mechanism 130 is immovably captured in plate hole 14 with fastener 160, and retaining mechanism 130 axially restrains fastener 160 relative to plate 12. Retaining mechanism 130 can pivot within hole 14 to allow multi-angle placement capabilities for fastener 160 as it is positioned through plate 10 and driven into the underlying bony structure.

Fastener 160 can be further driven into the underlying bony structure until head 166 is received in bore 134. Outer surface 172 contacts inner wall surface 144 of retaining mechanism 130. The taper angles of wall surface 144 and outer surface 172 can be configured to provide a locking arrangement to cause locking of bone screw 160 in retaining mechanism 130 when head 166 is seated in bore 134.

In another embodiment, head 166 can be sized relative to the opening formed by inner wall surface 144 to expand retaining mechanism 130 so that outer surface 132 contacts wall surface 18 of plate 12. Like retaining mechanism 30, the expansion of retaining mechanism 130 can be facilitated by a slot (not shown), which extends between inner wall surface 144 and outer surface 132.

In yet another embodiment, the taper angles of outer surface 172 of head 166 and inner wall surface 144 are not mismatched relative to one another. Thus, head 166 is not locked in retaining mechanism 30 when seated in bore 134. However, head 166 is sized to contact inner wall surface 144 to expand retaining mechanism 130 so that outer surface 132 contacts wall surface 18 of plate 12. Like retaining mechanism 30, the expansion of retaining mechanism 130 can be facilitated by a slot (not shown), which extends between inner wall surface 144 and outer surface 132.

It should be understood that implant 10 may comprise any orthopedic implant where it is desired to secure the implant to bone. In the form of bone plate 12, it may include any number of holes to receive any number of bone fasteners, and the plate holes may be situated in any arrangement along the plate. The other holes of the plate may be the same as hole 14 or may include various forms other than that discussed above for hole 14, such as an elongated slot form, a linear form, or a spherical recess adjacent the upper surface of the plate. Bone fasteners may be positioned in one or more of the other holes, and one or more anti-backout devices may be provided at any one or more of the other holes. The bone fasteners can also be positioned in various orientations relative to the plate, including fixed orientation and variable angle orientations. Furthermore, the plate may include various lengths, shapes and curvatures adapted for the particular implantation location that is contemplated. Plate 12 may include other structures to facilitate implantation at a particular location, such as spikes, ridges, interbody spacers or other components that engage or are positioned between one or more bony structures to which the plate is to be engaged.

It is contemplated that retaining mechanisms 30, 130 can have application with plates shaped and sized for the anterior cervical spine, and with spinal plates for other regions of the spine, including the cranial, thoracic, lumbar, and/or sacral portions of the spine. Retaining mechanisms 30, 130 can be employed with spinal plates adapted for attachment to various locations of the spine, including the anterior, oblique, anterolateral, lateral, and posterior portions of the spine. It is further contemplated that retaining mechanisms 30, 130 can have application in bone plates other than those used in spinal surgery. It is also contemplated that any one or combination of the plate holes can be provided with other retaining devices to prevent fastener back-out or without retaining devices at all.

While the invention has been illustrated and described in detail in the drawings and foregoing description, the same is to be considered as illustrative and not restrictive in character. All changes and modifications that come within the spirit of the invention are desired to be protected.

What is claimed is:

1. An implant system, comprising:
an implant attachable to a bony structure, said implant including a hole having a wall surface extending about a central axis, said wall surface being concavely curved between upper and lower surfaces of said implant;
a retaining mechanism including a cylindrical body extending between first and second ends and a bore through said body, said body including an outer surface convexly curved between said first and second ends, said retaining mechanism further including an inner wall surface about said bore having a thread profile formed therein with said thread profile extending in said inner surface in a direction from said first end toward said second end of said cylindrical body; and
a fastener positionable through said bore of said retaining mechanism, said fastener including an externally threaded shaft threadingly engaging said thread profile in said inner wall surface of said retaining mechanism as said threaded shaft passes through said bore of said retaining mechanism, said fastener including a non-threaded head at a proximal end of said shaft positioned in contact with said inner wall surface to expand said cylindrical body against said wall surface about said hole, wherein said head defines a first width at an outer surface thereof that contacts said inner wall surface of and to expand said cylindrical body of said retaining mechanism and said threaded shaft defines a second width greater than said first width, wherein said second width is a major diameter of said threads and said first width of said outer surface of said non-threaded head contacts said inner surface on said thread profile of said retaining mechanism to expand said cylindrical body into contact with said wall surface of said implant about said hole.

2. The system of claim 1, wherein said inner wall surface includes a third width that is less than said first width.

3. The system of claim 2, wherein said body includes a slot extending between said inner wall surface and said outer wall surface.

4. The system of claim 1, wherein said bore is tapered from said upper surface to said lower surface of said implant.

5. The system of claim 4, wherein said head of said fastener is tapered to fit within said tapered bore.

6. The system of claim 1, wherein:
said implant include a pair of channels extending into said implant from said upper surface on opposite sides of said hole, each of said channels opening at said upper surface of said implant and in communication with a centralized portion of said hole, said pair of channels forming an opening dimension into said hole at said upper surface that is greater than a second opening dimension into said hole around a remaining portion of said hole at said upper surface not occupied by said pair of channels; and
wherein in an insertion orientation of said retaining mechanism said bore extends transversely to said central axis and said channels receive said outer surface of said body and permit passage of said body into said centralized portion of said hole in said insertion orientation, said retaining mechanism further being movable in said hole from said insertion orientation to a fastener receiving orientation in said hole wherein said bore extends along said central axis and said retaining mechanism is located between said upper and lower surfaces of said implant.

7. An implant system, comprising:
an implant attachable to a bony structure, said implant including a hole extending between upper and lower surfaces of said implant along a central axis;
a retaining mechanism in said hole including a cylindrical body extending between first and second ends and a bore through said body, said body further including an internal thread profile in an inner wall surface extending about said bore in a direction from said first end toward said second end of said cylindrical body;
a fastener including a threaded shaft and a head at a proximal end of said shaft, said threaded shaft threadingly engaging said internal thread profile of said retaining mechanism as said threaded shaft is positioned through said bore, wherein:
said implant include a pair of channels extending into said implant from said upper surface on opposite sides of said hole, each of said channels opening at said upper surface of said implant and in communication with a centralized portion of said hole, said pair of channels forming an opening dimension into said hole at said upper surface that is greater than a second opening dimension into said hole around a remaining portion of said hole at said upper surface not occupied by said pair of channels; and
said body of said retaining mechanism includes an outer surface convexly curved between said first and second ends, wherein said retaining mechanism is inserted into said channels on said opposite sides of said hole of said implant with said bore of said retaining mechanism extending substantially transversely to said central axis of said hole so that said channels receive said outer surface of said body to pass said body into said centralized portion of said hole, said retaining mechanism further being moved in said channels from said substantially transverse orientation of said bore to said central axis to a fastener receiving orientation in said hole wherein said bore of said retaining mechanism extends along said central axis and said retaining mechanism is located between said upper and lower surfaces of said implant.

8. The system of claim 7, wherein said head is non-threaded and engages said inner wall surface of said retaining mechanism along said internal thread profile when received in said bore.

9. The system of claim 8, wherein said body of said retaining mechanism includes a slot extending between said inner wall surface and an outer surface of said body, and said non-threaded head contacts said inner wall surface of said retaining mechanism and radially expands said body of said retaining mechanism.

10. The system of claim 7, wherein said hole of said implant includes a wall surface concavely curved between said upper and lower surfaces, said centralized portion of said hole defining a maximum dimension of said hole in said implant.

11. The system of claim 7, wherein said head includes a first width and said threaded shaft includes a thread profile defining a second width greater than said first width.

12. The system of claim 7, wherein said cylindrical body includes a convexly curved outer surface between said first and second ends.

13. The system of claim 12, wherein said hole is defined by a wall surface having a concave curvature between said upper and lower surfaces of said implant, said concave curvature conforming to said convex curvature of said outer surface of said body.

14. The system of claim 7, wherein said implant is a bone plate.

15. A method for engaging a spinal plate along a spinal column, comprising;
positioning the plate along at least one vertebra, the plate including at least one hole and a retaining mechanism positioned in the at least one hole;
threadingly engaging a threaded shaft of a bone fastener to an internal thread profile that extends along an internal bore of the retaining mechanism in a direction in which the fastener advances through the retaining mechanism as the fastener is engaged to the at least one vertebra;
radially expanding the retaining mechanism with a non-threaded head at a proximal end of the fastener when the head is seated in the retaining mechanism, wherein the non-threaded head defines a first width at an outer surface thereof in contact with the retaining mechanism on the internal thread profile so that said non-threaded head radially expands the retaining mechanism and the threaded shaft defines a second width greater than the first width, wherein the second width is a major diameter of the threads; and
maintaining the non-threaded head in contact with an inner surface of the retaining mechanism that extends around the internal bore to contact the expanded retaining mechanism with the plate in the at least one hole to prevent the bone fastener from backing out of the at least one hole.

16. The method of claim 15, further comprising pivoting the retaining mechanism in the plate hole as the fastener is engaged to the at least one vertebra.

17. The method of claim 15, further comprising axially constraining the bone fastener in the at least one hole with the retaining mechanism.

18. The method of claim 15, wherein:
the plate includes a pair of channels extending into the plate from an upper surface of the plate, the channels being located on opposite sides of the at least one hole, each of the channels opening at the upper surface of the plate and are in communication with a centralized portion of the hole located between the upper surface of the plate and a lower surface of the plate opposite the upper surface, the pair of channels forming an opening dimension into the at least one hole at the upper surface that is greater than a second opening dimension into the at least one hole around a remaining portion of that at least one hole not occupied by the pair of channels, wherein the at least one hole extends along a central axis between upper and lower surfaces of the plate; and the retaining mechanism includes a body with an outer surface convexly curved between opposite first and second ends of the body, wherein in an insertion orientation of the retaining mechanism the internal bore extends transversely to the central axis and the pair of channels receive the outer surface of the body and permit passage of the body into the centralized portion of the hole in the insertion orientation, the retaining mechanism further being movable in the at least one hole from the insertion orientation to a fastener receiving orientation in the at least one hole wherein the internal bore extends along the central axis and the retaining mechanism is located between the upper and lower surfaces of the plate.

* * * * *